US012562263B1

(12) United States Patent
Browder et al.

(10) Patent No.: US 12,562,263 B1
(45) Date of Patent: Feb. 24, 2026

(54) METHOD AND SYSTEMS FOR GENERATING AN ENTITY DURATION VALUE WITHIN A GRAPHICAL USER INTERFACE

(71) Applicant: Signet Health Corporation, North Richland Hills, TX (US)

(72) Inventors: Blake Browder, Dallas, TX (US); Joy Figarsky, Little Rock, AR (US)

(73) Assignee: BH Operations, LLC, North Richland Hills, TX (US)

( * ) Notice: Subject to any disclaimer, the term of this patent is extended or adjusted under 35 U.S.C. 154(b) by 0 days.

(21) Appl. No.: 18/957,782

(22) Filed: Nov. 24, 2024

(51) Int. Cl.
| | |
|---|---|
| *G16H 40/20* | (2018.01) |
| *G06F 3/0482* | (2013.01) |
| *G06T 11/20* | (2006.01) |

(52) U.S. Cl.
CPC ........... *G16H 40/20* (2018.01); *G06F 3/0482* (2013.01); *G06T 11/206* (2013.01)

(58) Field of Classification Search
USPC ....................................................... 705/2–3
See application file for complete search history.

(56) References Cited

U.S. PATENT DOCUMENTS

| | | | |
|---|---|---|---|
| 7,664,659 | B2 | 2/2010 | Lancaster et al. |
| 8,972,295 | B2 * | 3/2015 | Johnson .............. G06F 3/04886 |
| | | | 705/37 |
| 9,569,723 | B2 | 2/2017 | Saeed |
| 10,142,255 | B1 * | 11/2018 | Pachon ............ G06Q 10/08355 |

| | | | |
|---|---|---|---|
| 10,957,450 | B2 | 3/2021 | Chattopadhyay et al. |
| 11,600,380 | B2 | 3/2023 | Martindale et al. |
| 12,007,870 | B1 * | 6/2024 | Jain ..................... G06F 11/3438 |
| 2008/0255880 | A1 * | 10/2008 | Beller .................... G06Q 10/00 |
| | | | 705/3 |

(Continued)

FOREIGN PATENT DOCUMENTS

| | | |
|---|---|---|
| JP | 2021026358 A | 2/2021 |
| KR | 20210113042 A | 9/2021 |

OTHER PUBLICATIONS

Gomes, S. (2014). Selection constructive based hyper-heuristic for dynamic scheduling (Order No. 28977243). Available from ProQuest Dissertations and Theses Professional. (2628776326). Retrieved from https://dialog.proquest.com/professional/docview/2628776326? accountid=131444 (Year: 2014).*

*Primary Examiner* — Bennett Stephen Erickson
(74) *Attorney, Agent, or Firm* — Caldwell Intellectual Property Law

(57) ABSTRACT

A system for generating an entity duration value within a graphical interface, wherein the system includes at least a computing device, a display device, a memory; a processor configured to: generate a display data structure, providing a plurality of visual elements associated with a plurality of node modules and at least an event handler, wherein: a first visual element linked to a first data module of a node module of the plurality of node modules; a second visual element linked to a second data module of at least an entity duration value; the first data module is configured to: receive first data corresponding to the node utilization interval; and execute the second data module; and the second data module is configured to: modify the node utilization interval; and generate the display data structure using the plurality of visual elements and the at least an event handler.

16 Claims, 9 Drawing Sheets

(56) References Cited

U.S. PATENT DOCUMENTS

2016/0210438 A1* 7/2016 Ohta ....................... G16H 40/60
2017/0161439 A1* 6/2017 Raduchel ............ H04W 12/033
2020/0185096 A1* 6/2020 Bantilan .............. H04L 67/535
2025/0087342 A1* 3/2025 Khosla ................... G16H 40/20

* cited by examiner

200a 208
216e   216f    212    216a
204
216b

October 7, 2024

216c
216d

Patient Information

216h

Diagnosis
Duration of Stay
First Visual Element

216k

216n

216i

Insurance Information

216j

216c 216d   216e   216f

216g

200b

208

216e   216f    212    216a

216b

204

October 7, 2024

216c
216d

Patient Information

Duration of Stay
Projected Duration
Second Visual Element

216l

Insurance Coverage

216m

216c 216d   216e   216f

216g

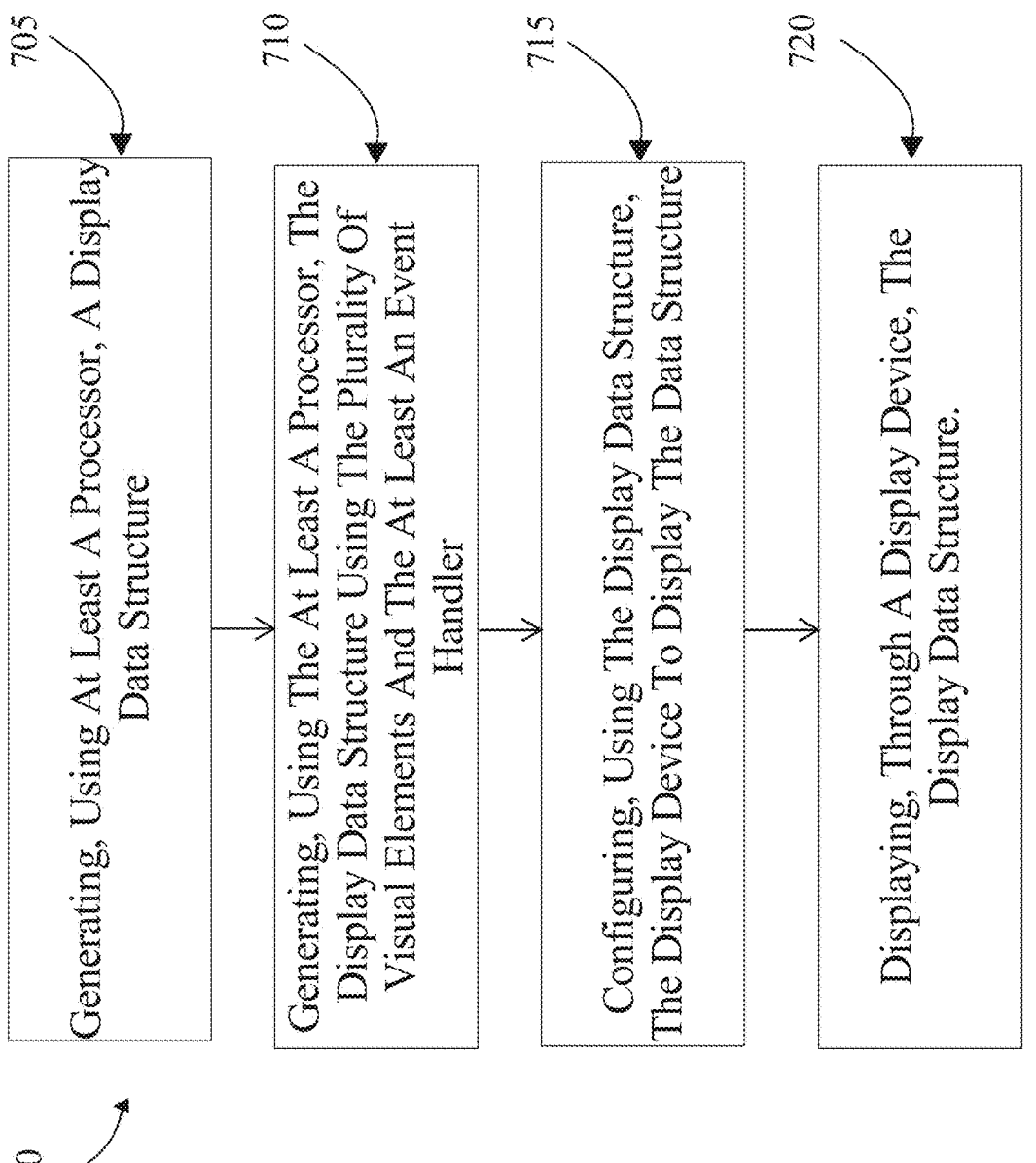

705 Generating, Using At Least A Processor, A Display Data Structure

710 Generating, Using The At Least A Processor, The Display Data Structure Using The Plurality Of Visual Elements And The At Least An Event Handler 715 Configuring, Using The Display Data Structure, The Display Device To Display The Data Structure 720 Displaying, Through A Display Device, The Display Data Structure.

METHOD AND SYSTEMS FOR GENERATING AN ENTITY DURATION VALUE WITHIN A GRAPHICAL USER INTERFACE

FIELD OF THE INVENTION

The present invention generally relates to the field of graphical user interfaces. In particular, the present invention is directed to generating an entity duration values within a graphical user interface.

BACKGROUND

Modern graphical user interfaces (GUIs) often lack adequate responsiveness when cross-referencing iteratively updated inputs. Furthermore, existing software may struggle to project accurate comparison data without relying on generated or simulated data, compromising reliability.

SUMMARY OF THE DISCLOSURE

In an aspect, a system for generating an entity duration value within a graphical interface, wherein the system includes at least a computing device, wherein the computing device comprises: a display device, wherein the display device displays a graphical user interface (GUI); a memory; a processor, communicatively connected to the memory, wherein the processor is configured to: generate a display data structure, wherein generating the display data structure further comprises: providing a plurality of visual elements associated with a plurality of node modules and at least an event handler, wherein: a first visual element of the plurality of visual elements is linked to a first data module of a node module of the plurality of node modules; a second visual element of the plurality of visual elements is linked to a second data module of at least an entity duration value; the first data module is configured to: receive first data corresponding to the node utilization interval as a function of the at least an entity duration value and the plurality of node modules; and execute, using a first control structure, the second data module; and the second data module is configured to: modify the node utilization interval as a function of the at least an entity duration value; and generate the display data structure using the plurality of visual elements and the at least an event handler; and configure, using the display data structure, the display device to display the data structure.

In another aspect, a method for generating an entity duration value within a graphical interface, wherein the method includes generating, by at least a processor, a display data structure, wherein generating the display data structure further comprises: providing a plurality of visual elements associated with a plurality of node modules and at least an event handler, wherein: a first visual element of the plurality of visual elements is linked to a first data module of a node module of the plurality of node modules; a second visual element of the plurality of visual elements is linked to a second data module of at least an entity duration value; the first data module is configured to: receive first data corresponding to the node utilization interval as a function of the at least an entity duration value and the plurality of node modules; and execute, using a first control structure, the second data module; and the second data module is configured to: modify the node utilization interval as a function of the at least an entity duration value; and generate the display data structure using the plurality of visual elements and the at least an event handler; and configure, using the display data structure, the display device to display the data structure.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 7 is a block diagram of an exemplary embodiment for a method for generating an entity duration value within a graphical user interface.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for In an aspect, a system for generating an entity duration value within a graphical interface, wherein the system includes at least a computing device, wherein the computing device comprises: a display device, wherein the display device displays a graphical user interface (GUI); a memory; a processor, communicatively connected to the memory, wherein the processor is configured to: generate a display data structure, wherein generating the display data structure further comprises: providing a plurality of visual elements associated with a plurality of node modules and at least an event handler, wherein: a first visual element of the plurality of visual elements is linked to a first data module of a node module of the plurality of node modules; a second visual element of the plurality of visual elements is linked to a second data module of at least an entity duration value; the first data module is configured to: receive first data corresponding to the node utilization interval as a function of the at least an entity duration value and the plurality of node modules; and execute, using a first control structure, the second data module; and the second data module is configured to: modify the node utilization interval as a function of the at least an entity duration value;

and generate the display data structure using the plurality of visual elements and the at least an event handler; and configure, using the display data structure, the display device to display the data structure.

Figure 1:
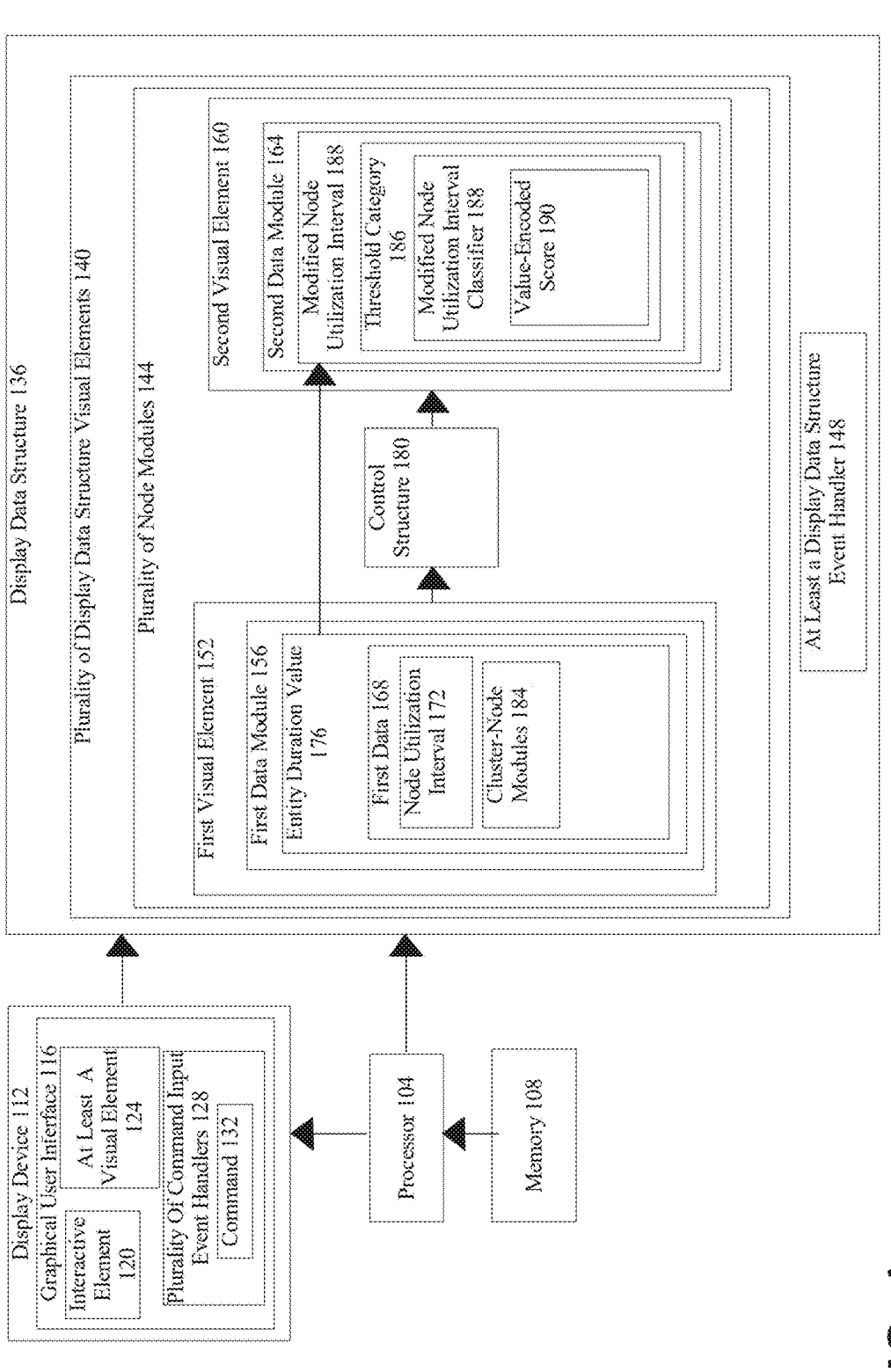
FIG. 1 is a flow diagram illustrating a system for generating an entity duration value within a graphical interface.

Referring now to FIG. 1, an exemplary embodiment of a system for generating an entity duration value within a graphical user interface is illustrated. System 100 may include a processor 104 communicatively connected to a memory 108. As used in this disclosure, "communicatively connected" means connected by way of a connection, attachment, or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor 104. In one or more embodiments, data is transferred from secondary to primary memory wherein processor 104 may access the information from primary memory.

Still referring to FIG. 1, system 100 may include a database. The database may include a remote database. The database may be implemented, without limitation, as a relational database, a key-value retrieval database such as a NOSQL database, or any other format or structure for use as database that a person skilled in the art would recognize as suitable upon review of the entirety of this disclosure. The database may alternatively or additionally be implemented using a distributed data storage protocol and/or data structure, such as a distributed hash table or the like. The database may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, system 100 may include and/or be communicatively connected to a server, such as but not limited to, a remote server, a cloud server, a network server and the like. In one or more embodiments, the computing device may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by the system computing device. In one or more embodiments, computing device may transmit processes to server wherein computing device may conserve power or energy.

Further referring to FIG. 1, system 100 may include any "computing device" as described in this disclosure, including without limitation a microcontroller, microprocessor, digital signal processor (DSP) and/or system on a chip (SoC) as described in this disclosure. System 100 may include, be included in, and/or communicate with a mobile device such as a mobile telephone or smartphone. System 100 may include a single computing device operating independently, or may include two or more computing devices operating in concert, in parallel, sequentially or the like; two or more computing devices may be included together in a single computing device or in two or more computing devices. System 100 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. System 100 may include one or more computing devices dedicated to data storage, security, distribution of traffic for load balancing, and the like. System 100 may distribute one or more computing tasks as described below across a plurality of computing devices of computing device, which may operate in parallel, in series, redundantly, or in any other manner used for distribution of tasks or memory between computing devices. System 100 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. In a non-limiting embodiment, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a display device 112 wherein display device 112 displays a graphical user interface 116. A "graphical user interface," as used herein, is a graphical form of user interface that allows users to interact with electronic devices. In some embodiments, GUI 116 may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages, and the like may be represented using a small picture in a graphical user interface. In a non-limiting embodiment, links to decentralized platforms as described in this disclosure may be incorporated using icons. Using an icon may be a fast way to open documents, run programs etc. because clicking on them yields instant access.

As used in this disclosure, an "interactive element" is a component within a system, interface, or device that allows a user to engage with and influence the system's behavior or output through actions. In a non-limiting example, the actions may include clicking, touching, or inputting data. Without limitation, the interactive element 120 may respond dynamically to an input, enabling real-time feedback or control over system functions. In a non-limiting embodiment, without limitation the interactive element 120 may include buttons, sliders, input fields, or menus in software interfaces, as well as physical controls like switches or touchscreens in hardware devices. Each interactive element of a plurality of interactive elements may comprise an event handler configured to detect an interaction and generate response data as a function of the interaction.

As used in this disclosure, a "visual element" is a component or feature within a system, display, or interface that conveys information through visual means. In a non-limiting example, the visual element 124 may include text, images, icons, shapes, colors, and/or other graphical components designed to be perceived by the user. In a non-limiting example, the visual element 124 may aid in communication, navigation, and/or interaction with the system. Without limitation, the visual element 124 may be used to enhance user experience, guide behavior, and/or represent data visually in an intuitive or informative way. A visual element 124 may include any data transmitted to display device, client device, and/or graphical user interface 116. In some embodiments, visual element 124 may be interacted with. In a non-limiting embodiment, visual element 124 may include an interface, such as a button or menu. In some embodiments, visual element 124 may be interacted with using a user device such as a smartphone, tablet, smartwatch, or computer.

Still referring to FIG. 1, processor 104 displays, using the graphical user interface 116 a plurality of command input event handlers 128 wherein a command 132 in the plurality of command input event handlers 128 corresponds to the at least a visual element 124. As used in this disclosure, a "command input event handler" is a is a structured list of tasks, instructions, and/or operations that are organized in a specific sequence. In a non-limiting example, the plurality of command input event handlers 128 may include at least a command 132. As used in this disclosure, a "command" is an instruction or directive given to a person, system, device, and/or process to perform a specific action or task. Without limitation, the command 132 may initiate an operation, alter system behavior, or trigger a response, and may be issued manually by a user or automatically by a program or system. In a non-limiting example, the command 132 may control hardware functions, execute software routines, or interact with external systems, and may be part of a sequence within the plurality of command input event handlers 128. In a non-limiting example, the command 132 may be awaiting execution or confirmation from a user. In a non-limiting example, the plurality of command input event handlers 128 may function as a checklist where each command 132 or task may be processed, executed, or marked as completed by the user or system.

Continuing reference to FIG. 1, at least a processor 104 may be configured to generate a display data structure 128. As used herein, a "display data structure" refers to a data structure designed to visually present information in an interactive manner. Examples of information generated through display data structure 136 may include information relating to patient hospital stays, incorporating key metrics, and color-coded indicators for rapid assessment. The display data structure 136 may include fields such as unique Patient ID, identifying each patient individually, and a Current Length of Stay (LOS) field, representing the number of days the patient has been hospitalized. Additionally, it may include an Average Payor Length (APL) field, denoting the typical reimbursable duration according to the patient's specific payor, which may be dynamically adjusted based on factors like age, diagnosis, or payor-specific policies. For instance, Age-Adjusted APL may apply a standard LOS metric based on age brackets, such as 6-8 days for adults and 12 days for seniors, while Diagnosis-Specific APL may modify the average LOS based on particular diagnoses, allowing for tailored projections. A Color Indicator (Status) may provide visual cues, with Green indicating stays within reimbursable limits (e.g., days 1-8), Yellow signaling slightly extended stays, and Red highlighting stays that significantly exceed these limits. This structure may update in real-time as patient data evolves, enabling healthcare providers to monitor LOS relative to payor policies efficiently, optimize discharge planning, and ensure compliance with reimbursement guidelines.

Continuing reference to FIG. 1, generating display data structure 136 may include providing a plurality of display data structure visual elements 140 associated with a plurality of node modules 144 and at least display data structure an event handler 148. The plurality of display data structure visual elements 140 may include various interactive or static components designed to convey critical information, such as icons, charts, or color-coded indicators that visually communicate the status or progression of patient data within the user interface. The plurality of display data structure visual elements 140 may correspond to the plurality of node modules 144. As used herein, a "plurality of node modules" refers to data structures comprising health and hospital-related information. In a non-limiting embodiment, the plurality of node modules 144 may include patient demographics, medical history, insurance information, current diagnoses, treatment plans, length-of-stay metrics, and the like. Each node module of the plurality of node modules 144 may be associated with real-time patient information that dynamically updates in response to new data inputs. Patient data may be received from an electronic health record. At least a display data structure event handlers 148 may be used to manage user interactions with the interface, allowing for updates, modifications, or retrieval of specific patient data upon user command. As used herein "Display data structure event handlers" are functions or routines within a software application that respond to specific user interactions or system-generated events related to a visual data structure on a display. The at least a display data structure event handler 148 may response to actions such as clicking, hovering, or selecting a visual element, thereby triggering relevant information displays or adjustments to the interface.

Still referring to FIG. 1, a first visual element 152 of the plurality of display data structure visual elements 140 may be linked to a first data module 156 of a node module of the plurality of node modules 144. As used herein, the first visual element 152 refers to an interactive or static display component within the user interface that is directly associated with core patient information, such as identifying details or health status indicators. For instance, the first visual element 152 may take the form of a patient profile icon, a health status bar, or a color-coded field displaying the patient's current condition, demographic details, vital statistics, insurance information, and the like. The linkage between the first visual element 152 and the first data module 156 may allow for real-time reflection of updates or changes in patient information. As used herein, "a data module" is a structured component within a system that encapsulates specific sets of data and the associated functions or methods used to handle that data. It serves as a container for organizing, storing, and managing related data elements, often making it easier to access, modify, and process the data within a larger framework or application. Data modules may represent various types of information, such as patient records, financial transactions, or sensor readings, depending on the system's purpose. In an embodiment, any updates in the patient's medical data, such as changes in diagnosis, treatment plans, or length of stay, may automatically adjust the information displayed in the first visual element 152. In an embodiment, a second visual element 160 of the plurality of visual elements is linked to a second data module 164 of a node module of the plurality of node modules. As used herein, the "second visual element" refers to an interactive or static display component within the user interface that is directly associated with insurance-related information. In an embodiment, the second visual element 160 may be configured as a duration bar, chart, or other visual indicator that displays the reimbursable period in green (e.g., 6-8 days for adults, 12 days for seniors) with additional days shown in yellow or red if the stay extends beyond the reimbursable limit.

Continuing reference to FIG. 1, the first data module 156 may be configured to receive a first data 168 corresponding to a node utilization interval 172 as a function of the at least an entity duration value 176 and the plurality of node modules 144. As used herein, a "node utilization interval" is a measurement of hospital resource utilization specific to each patient. As used herein, first data 168 corresponding to the node utilization interval 172 refers to the initial data inputs received by the system that quantify and define the duration of a patient's stay in the hospital. In a non-limiting embodiment, first data 168 may include timestamps, admission and discharge dates, or real-time updates reflecting the length of the patient's current hospitalization. By associating the entity duration value 176 with this visual display, the interface can promptly alert providers when a patient's stay nears or exceeds coverage limits, facilitating timely discharge planning and clear communication regarding potential out-of-pocket costs. As used herein, an "entity duration value" is a data metric representing the reimbursable duration of a hospital stay covered by a specific insurance provider (or payor). This value specifies the maximum number of days that the insurance provider will fund for a patient's hospital admission, typically based on factors such as patient demographics (e.g., age) or diagnosis type. For example, the entity duration value might be set at 6-8 days for adult patients or 12 days for seniors, depending on the policy and condition. In an embodiment, entity duration value 176 allow healthcare providers to track hospital stays against coverage limits in real time, facilitating discharge planning and helping to avoid non-reimbursable expenses.

In an embodiment, at least a processor 104 may be configured to map an interval of the node utilization interval 172 representing the actual length of stay of a patient against the at least an entity duration value 176 representing the reimbursable period set by an insurance policy. In an embodiment, first data 168 may be iteratively updated as a function of new data that becomes available. In an embodiment, the node utilization interval 172 may be dynamically adjusted as a function of a corresponding determination value. Examples of corresponding determination values may include changes in familial history, changes in occupational data, changes in insurance data, changes in diagnoses, and the like. In an embodiment, this interval allows system 100 to calculate and display, in real time, whether a patient's stay remains within the insurance covered duration, or if it is nearing or exceeding the insurance limits. In a non-limiting embodiment, as the first data module 156 receives first data 168, either periodically or continuously, the node utilization interval 172 may be updated to reflect any changes in the patient's length of stay or adjustments in insurance coverage parameters. By calculating the stay as a function of the entity duration value, the node utilization interval enables the system to detect when the patient's stay is nearing or exceeding the payor's reimbursable period, thus facilitating preemptive adjustments in care management or discharge planning.

In an embodiment, first data 168 may be received through the use of a chatbot interface presented through the user interface. As used herein, a "chatbot interface" refers to a user interface that allows users to interact with system 100 through natural language input, typically in the form of text or speech. In an embodiment, the chatbot interface enables users to issue queries, provide commands, or make specific requests, to which system 100 is configured to respond with relevant data or actions. The chatbot interface may utilize Natural Language Processing (NLP) to interpret and process the user's first data inputs. NLP is a subfield of artificial intelligence focused on enabling computers to process, understand, and generate human language. NLP systems consist of multiple layers of text analysis, including tokenization (breaking down a query into individual components such as words or phrases), part-of-speech tagging (identifying grammatical elements in the query), syntactic parsing (understanding sentence structure), and semantic analysis (extracting the meaning and intent behind the query). In an embodiment, the chatbot interface may incorporate advanced NLP techniques, such as word embeddings (e.g., Word2Vec, GloVe), which map words to vector representations to capture context and meaning, as well as transformer-based architectures (e.g., BERT, GPT), which allow the system to handle more complex queries that depend on contextual relationships between words. The response may be structured in a conversational manner, mimicking human-like interaction to improve the user experience. Through the chatbot interface, users can seamlessly interact with system 100, which leverages NLP to intelligently understand, process, and respond to queries in real time.

Still referring to FIG. 1, first data module 156 may be configured to execute, using a control structure 180, the second data module 164. As used herein, a "control structure" refers to programmed set of instructions, rules, or logical conditions configured to manage and direct the execution of operations within a system. In an embodiment, the first control structure 180 may include conditional statements, looping structures, function calls, or event-driven triggers that dictate how and when data is transferred or processed between modules. For example, the control structure 180 may be designed to conditionally execute the second data module 164 upon detecting specific conditions, such as the receipt of updated patient stay data or a trigger event indicating a nearing of the insurance coverage limit. It may also handle asynchronous operations, allowing parallel data processing without interrupting other system functions. In this configuration, the first control structure 180 may be implemented as a set of programmed instructions, logical conditions, or algorithms that enable the first data module to initiate, control, and govern the execution of operations by the second data module. Upon activation, the control structure 180 may direct the first data module 156 to initiate specific commands or invoke functional routines within the second data module 164, enabling the seamless transfer, manipulation, or analysis of data associated with the patient's insurance parameters and stay-related metrics. This operational flow may involve initiating data retrieval, synchronization, or computational functions, wherein the second data module 164 is engaged to process the entity duration value and other insurance-related data against the node utilization interval derived from the patient's actual stay information. In a non-limiting embodiment, the control structure may enable conditional execution based on threshold criteria, such as alerting when the patient's stay nears the reimbursable limit, or may employ event-driven triggers to update the display structure in response to changes in the patient's length of stay or updates in insurance coverage parameters. In some embodiments, the first control structure may also facilitate asynchronous data processing, allowing the first data module to handle real-time updates while the second data module performs background calculations, thereby enhancing the system's efficiency and ensuring real-time availability of critical data points for healthcare providers.

In an embodiment, receiving the first data 168 corresponding to the node utilization interval may include selecting cluster-node modules 184 wherein each cluster-node module comprises at least one common parameter shared across individual node modules. In an embodiment, a cluster-node module 184 functions as an aggregated collection or grouping of node modules that are associated through a common parameter, such as patient demographic factors, diagnosis categories, or insurance policy attributes. Cluster-node modules 184 may be dynamically driven by the system 100 based on operational needs or user-defined criteria, such as a specific age group or diagnosis type that impacts the entity duration value associated with each patient's reimbursable length of stay. For instance, a cluster-node module 184 may group patients aged 65 and older or patients with a specific medical condition that influences the length of stay covered by insurance. Through this clustering, the system enables the first data module 156 to receive relevant first data 168 by aligning the node utilization interval 172 with parameters that impact hospital resource utilization and insurance reimbursement policies. In an embodiment, selecting the cluster-node modules may involve the use of a cluster-node machine learning model that has been trained on a comprehensive set of cluster-node training data. This machine learning model may be configured to analyze and identify correlations between individual node modules and broader cluster-node modules based on shared characteristics or parameters. In an embodiment, the cluster-node training data may include a diverse set of node modules, each with parameters such as age, diagnosis type, or insurance coverage limits, example node modules, historical cluster-node modules, and the like, allowing the model to generalize across various patient profiles.

Still referring to FIG. 1, second data module 164 may be configured to modify the node utilization interval 188 as a function of the at least an entity duration value 176. In an embodiment, the second data module 164 may be configured as a processing unit that dynamically adjusts the node utilization interval 172 according to specific criteria or constraints defined by the entity duration value 176, which can represent the maximum reimbursable days covered by the patient's insurance provider. In an embodiment, the second data module 164 may utilize conditional algorithms to evaluate the node utilization interval 172 against the entity duration value 176. If the patient's length of stay approaches or exceeds the reimbursable duration, the second data module 164 may invoke adjustments that modify the interval to flag the excess days, or mark segments of the interval as non-reimbursable. Additionally, the second data module 164 may employ feedback loops and event-driven triggers to modify the node utilization interval 172 in real time. This could include recalculating the interval in response to specific events, such as an extended stay, a revised insurance policy, or adjustments based on age or diagnosis-related criteria affecting reimbursement limits. In an embodiment, the second data module may also incorporate a modification machine learning algorithms trained using modification training data configured to correlate historical data such as historical entity duration values, utilization values, historical first data 168, patient data, insurance data, and the like to necessary modifications to the node utilization interval. The modification machine learning model may additionally be iteratively trained using feedback on the effectiveness of the predicted outputs generated.

In an embodiment, the second data module 164 may employ clustering algorithms or classifiers to assign a patient to a relevant cluster based on specific features of their data. This clustering can operate either in a supervised or unsupervised manner. In a supervised approach, the clustering model is trained with labeled data, where each data point includes predefined cluster labels (e.g., high-risk, medium-risk, low-risk groups). This allows the clustering algorithm may learn patterns associated with specific cluster labels and accurately assign new patients to these predefined clusters. In an unsupervised approach, the clustering algorithm may receive unlabeled data and group patients into clusters based on detected similarities, even if the exact data points differ. Here, patients can be clustered based on similar characteristics (e.g., age, diagnosis, length of stay trends) without requiring matching data across all parameters, allowing the system to adapt to a broader range of patient profiles. The second data module 164 may further integrate a machine-learning model capable of projecting an appropriate node utilization interval tailored to the individual patient. In one embodiment, the model may receive the cluster assignment for a patient and, based on this classification, output a projected utilization interval. The training data for this model may include historical patient data, utilization intervals, and relevant entity duration values, allowing the model to learn optimal intervals based on similar patient clusters. Alternatively, the system may be configured with separate instances of the machine-learning model, each one specifically trained for a particular cluster. This approach enables finer tuning, as each model is exclusively optimized for its respective cluster, improving accuracy for a defined patient subset. For example, one model may be trained to project utilization intervals for high-risk patients, while another is dedicated to low-risk cases. Each model would utilize training data specific to its cluster, selected from historical datasets of patients within that group, including cluster-specific parameters such as average length of stay, reimbursement caps, and clinical diagnoses. This targeted training approach ensures that each machine-learning model is precisely aligned with the needs of its patient cluster, enhancing the system's ability to generate accurate and relevant utilization intervals. The second data module 164 may also incorporate modification machine-learning algorithms trained on modification training data designed to correlate historical entity duration values, utilization intervals, and patient data with necessary adjustments to the node utilization interval. The modification model may be iteratively trained using user feedback on the effectiveness of predicted intervals, allowing for continuous refinement. Through event-driven triggers and feedback loops, the model could modify the utilization interval in real-time, recalculating the interval if new patient information arises-such as extended stays, policy changes, or demographic factors affecting reimbursement limits-ensuring that node utilization intervals are optimally tailored and dynamically updated.

Continuing reference to FIG. 1, at least a processor 104 may be configured to generate the display data structure 136 using the plurality of display data structure visual elements 140 and the at least an at least a display data structure event handler 148. Processor 104 may generate the display data structure 136 by selecting and positioning visual elements of the plurality of display data structure visual elements 140, which may include icons, indicators, graphs, or color-coded status bars. As discussed above, each visual element of the plurality of visual elements may reference specific data points or metrics, such as patient length of stay, insurance coverage limits, and reimbursement eligibility, to visually convey critical information to users. Processor 104 may further customize the display of these elements based on user preferences, real-time data updates, or preset formatting parameters to ensure clarity and relevance. In an embodiment processor 104 may be configured to continuously monitor for updates within the at least an at least a display data structure event handler 148 such as events triggered by user actions and, upon detection, execute corresponding event handler routines. These routines may include updating visual elements, adjusting data displays, or retrieving additional information, allowing the display data structure to adapt fluidly to user inputs. In an embodiment. In an embodiment, processor 104 may leverage data-binding mechanisms to achieve synchronization of real-time data from multiple node modules with the plurality of display data structure visual elements 140 present within the display data structure 136 These data-binding mechanisms may allow processor 104 to establish connections between data sources, such as the node utilization interval 172, and the plurality of display data structure visual elements 140 like indicators, charts, or color-coded bars. This setup may enable dynamic updates in the display structure. For example, processor 104 may bind the node utilization interval 172 representing the length of a patient's stay in the hospital, to a visual bar indicator. This visual element may then continuously update in real time to reflect changes in the patient's hospital stay duration. As each additional day of stay is recorded, the processor may automatically adjust the bar indicator's display to show progression over time, allowing users to see the patient's current length of stay. This bar indicator may be color-coded to provide a clear visual representation of the hospital stay in relation to the entity duration value 176. For example, as the patient's stay approaches the reimbursable limit, the bar indicator might shift from green to yellow to alert healthcare providers of an impending limit. If the stay exceeds the reimbursable days, the color could turn red, signaling that the patient's stay has moved beyond what is covered by insurance. These color transitions may be automatically handled by processor 104 through conditional logic embedded within the data-binding mechanism, allowing the display to react instantly to data changes. Furthermore, processor 104 may implement bi-directional data binding to enable real-time updates in both directions, where any adjustments made within the display interface (such as recalculating an estimated discharge date or adjusting the entity duration value based on policy updates) can also update the source data in relevant node modules. In addition, processor 104 may incorporate event-driven data-binding methods to minimize resource usage, updating only those visual elements affected by data changes, rather than refreshing the entire display structure. For example, system 100 may track event triggers such as a change in the entity duration value 176, triggering a refresh of the visual bar indicator only when there is a change in insurance coverage or patient stay duration. In an embodiment, the application of a data mask to patient stay data may serve to generate a visual color representation based on the length of each patient's stay. This data mask may function as a mapping tool, potentially translating different stay lengths into corresponding color values, which could facilitate quick visual insights into durations. The data mask itself may be derived in one of two ways. In certain cases, an ML model responsible for producing node utilization interval data might output a customized data mask tailored to the specific patient, allowing for a more personalized and potentially accurate color representation. Alternatively, the processor may determine the appropriate data mask based on the node utilization interval data, applying a standardized mapping to visualize stay lengths.

In an embodiment, generating the display data structure 136 may include classifying the modified node utilization interval into a threshold category 186. As used herein, a "threshold category" refers to a predefined classification level used to assess and categorize specific data values based on their proximity to critical limits or conditions. This classification process may assign the modified node utilization interval 172, representing the current duration of a patient's hospital stay, to predefined threshold categories that reflect different levels of urgency or compliance relative to insurance reimbursement constraints. The threshold categories may be defined based on specific criteria and may include classifications such as "within reimbursable period," "nearing reimbursable limit," and "exceeds reimbursable period." Each category can correspond to a unique visual representation within the display data structure, such as distinct color codes (e.g., green for within limits, yellow for nearing limit, and red for exceeding limit), icons, or alert signals. These visual cues provide healthcare providers with an immediate understanding of the patient's stay relative to allowable insurance coverage, supporting efficient decision-making regarding discharge planning or care adjustments. Processor 104 may execute this threshold classification through a combination of conditional logic and predictive algorithms that dynamically evaluate the node utilization interval. In an embodiment, if the interval falls within a safe range well below the entity duration value, it may be automatically classified into the "within reimbursable period" category. As the interval approaches the upper bound of the entity duration value, the system may reclassify it into a "nearing reimbursable limit" category, triggering visual cues or automated notifications to alert staff of the upcoming coverage limit. If the interval exceeds the reimbursable duration, it is then classified into the "exceeds reimbursable period" category, signaling a potential cost liability.

In an embodiment, classifying the modified node utilization interval comprises a modified node utilization interval classifier 188 configured to correlate the at least a modified node utilization interval and at least an entity duration value. The modified node utilization interval classifier 188 may involve training data including historical node module data, patient demographics, historical first data, example modifications to the node utilization interval and the like. In an embodiment, the training process may employ feature engineering techniques, where specific features or predictor variables are selected, created, or transformed to maximize the classifier's ability to discern between threshold categories effectively. For instance, features such as "percentage of reimbursable duration utilized" or "variance in stay duration for specific diagnoses" can be derived to enhance the classifier's interpretive accuracy. In an embodiment, reinforcement learning techniques may be applied in certain training scenarios, where the classifier is rewarded or penalized based on the accuracy of its classifications relative to actual outcomes in real-world settings. Over multiple iterations, the modified node utilization interval classifier 188 may learn to refine its decision boundaries and adjust its internal classification criteria to achieve higher precision, particularly in complex cases where the reimbursement policy may vary based on patient conditions, treatment plans, or other variable factors. In an embodiment, the modified node utilization interval classifier may undergo continuous or incremental learning, where it may be periodically retrained on new data or updated with live feedback from system outputs. For instance, if the classifier's classification accuracy is monitored in a production environment, feedback data may be fed back into the model to fine-tune its performance. In an embodiment, generating the display data structure 136 may include assigning a value-encoded score 190 for each modified node utilization interval as a function of the modified node utilization interval classifier. As used herein, a "value-encoded score" is a numerical or categorical score that has been transformed or encoded to represent specific values for easier interpretation, analysis, or processing. This encoding might map scores onto a particular scale, range, or set of categories that have meaningful representations in a given context. For example, a value-encoded score could convert a raw performance score into a color-coded scale (e.g., high scores=green, medium scores=yellow, low scores=red) or map it onto predefined intervals (e.g., 1-10="low," 11-20="medium," 21-30="high"). In an embodiment, determining the value-encoded score, may include the modified node utilization interval value classifier configured to analyze and categorize the interval by assessing various factors such as the length of the hospital stay relative to the entity duration value, patient demographic information, and specific insurance parameters. Based on this analysis, the modified node utilization interval classifier may assign each modified node utilization interval to a risk or priority category, which then may be converted into a numeric or categorical score. For example, intervals that fall well within the reimbursable limit may receive a lower score, indicating low priority or urgency, while those nearing or exceeding the reimbursable duration may receive a higher score, signaling greater financial risk or urgency for discharge planning.

Continuing reference to FIG. 1, the system of claim 1 may be configured such that at least one processor is further enabled to receive, at the display device, an activation of at least one event handler, where this activation may involve receiving an input corresponding to at least one visual element among a plurality of visual elements linked to the event handler. Upon receiving this activation, the processor may execute at least one algorithm module associated with the activated event handler. This execution may include engaging an image processing module. An identification process may involve actively monitoring the algorithm's execution flow, cross-referencing expected outputs with actual results, and detecting any deviations or discrepancies that suggest a malfunction or inefficiency. The identification mechanism may include fault detection algorithms, real-time error logging, or diagnostic codes that may help pinpoint specific errors. In an embodiment the system may indicate an algorithm correction which may include generating and displaying suggested corrective actions or adjustments, potentially including automated or guided steps to resolve the error. The correction indication process may incorporate feedback loops that automatically adjust parameters or rerun certain parts of the algorithm, aiming to restore accurate functionality. Alternatively, the system may provide a notification or visual indicator that guides a user through the correction process, detailing specific actions to rectify the identified error.

With continued reference to FIG. 1, the at least a processor 104 may configure, using the display data structure, the display device to display the data structure. In an embodiment, utilizing the display data structure, processor 104 may first retrieve or organize the underlying data points, such as value-encoded scores, node utilization intervals 172 and threshold categories, and the like, structuring them according to the predefined display format. This structured data is then aligned with the designated visual elements of the plurality of display data structure visual elements 140, including icons, color-coded bars, numeric labels, and alert indicators, ensuring that each element accurately represents real-time information relevant to patient length of stay and reimbursement constraints. In some embodiments, processor 104 may also incorporate interactive elements-such as touch-enabled components, filters, or drill-down options-into the display data structure, allowing users to explore specific data points in more detail.

With continued reference to FIG. 1, The system may be configured to display, through the display device 112, the display data structure 136. In an embodiment, the processor may employ adaptive layout algorithms that adjust the arrangement of the display data structure 136 based on the type of data being displayed, screen size, and user interaction patterns. For example, critical data points—such as entity duration value 176 and current node utilization intervals 172—may be prominently positioned at the top of the display, ensuring high visibility and quick access. Additionally, the display device may use responsive design techniques that automatically reorganize visual elements to fit different orientations (e.g., portrait or landscape mode) or display sizes, such as when used on various devices like tablets, desktops, or smartphones. In an embodiment, the display may incorporate color-coded indicators and layered visual cues to communicate the status of each data point.

Figure 2A:
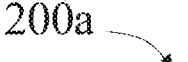
FIG. 2A is an exemplary illustration of a graphical user interface.

Referring now to FIG. 2A, an exemplary illustration 200a of a graphical user interface. In an embodiment, the graphical user interface 204 may be displayed using a downstream device 208. In an embodiment, the graphical user interface 204 may include at least a visual element 212. In an embodiment, the visual element 212 may include an interactive element 216. In an embodiment the interactive element 216 may allow a user to engage directly with the graphical user interface 204 through a variety of actions.

In an embodiment, the interactive element 216a-i may include a settings gear 216a, a profile icon 216b, a sorting icon 216c, a folder 216d, a new task icon 216e, a find icon 216f, an edit icon 216g, a check box icon 216h, a scroll bar 216i, text description 216j, and the like.

In an embodiment, the interactive element 216 may include a settings gear 216a. In an embodiment, the settings gear 216a may enable users to access the system or application cation settings where they may modify preferences and configurations. Without limitation, by clicking on the settings gear 216a, users may adjust features like notifications, display options, account details, and the like. In an embodiment, the settings gear 216a may represent control over personalizing the environment within the application. In an embodiment, the settings gear 216a may ensure that users can customize their experience to meet their specific needs.

In an embodiment, the interactive element 216 may include a profile icon 216b, which may allow users to access their personal profile settings. In an embodiment, the profile icon 216b may link to a page where users may view and edit their personal information, such as their name, contact details, or profile picture. In an embodiment, the profile icon 216b may make it simple for users to manage their account and view related data quickly. In an embodiment, the profile icon 216b may be placed in a convenient location, allowing easy access to account settings. In an embodiment, the profile icon 216b may help users maintain control over their profile, ensuring that their information stays up-to-date.

In an embodiment, the interactive element 216 may include a sorting icon 216c, which may allow users to organize data based on specific criteria. In an embodiment, the sorting icon 216c may be useful when dealing with large datasets or lists that need to be filtered or reordered. Without limitation, by clicking the sorting icon 216c, users may arrange items by various attributes such as date, name, priority, and the like. In an embodiment, the sorting icon 216c may simplify the process of locating specific information, making the interface more efficient to use. In an embodiment, the sorting icon 216c may ensure that users can easily customize how they view and interact with the content.

In an embodiment, the interactive element 216 may include a folder icon 216d, which may represent access to a file or document management system. Without limitation, by clicking on the folder icon 216d it may open a directory or list of stored files, allowing users to organize their content within the application. In an embodiment, the folder icon 216d may be essential for managing documents, media, or other file types efficiently. In an embodiment, the folder icon 216d may be associated with file storage and navigation, making it a familiar and intuitive tool for users. In an embodiment, the folder icon 216d may aid in keeping information organized and accessible within the system.

In an embodiment, the interactive element 216 may include a new task icon 216e, which may allow users to create or add a new item to their task list or project. In an embodiment, the new task icon 216e may provide a quick way for users to input new assignments or goals, streamlining task management. In an embodiment, the new task icon 216e once clicked, may open a form or prompt where users may specify details about the new task. In an embodiment, the new task icon 216e may help users stay organized by adding tasks efficiently as they arise. In an embodiment, the new task icon 216e may be a valuable tool for productivity, helping users keep track of their to-do lists.

In an embodiment, the interactive element 216 may include a find icon 216f, which may function as a search tool for locating specific information within the application. In an embodiment, the find icon 216f may allow users to quickly search through data, files, or content to pinpoint exactly what they need. In an embodiment, the find icon 216f may be especially useful in applications that manage large volumes of information or files. In an embodiment, the find icon 216f may enhance efficiency by reducing the time spent manually browsing through content. Continuing, by providing a fast search function, users may access information more quickly and effectively.

In an embodiment, the interactive element 216 may include an edit icon 216g, which may enable users to modify or update existing content within the application. Continuing, by clicking on the edit icon 216g, it may bring users to an editable version of the item, such as a text document, task, or file. In an embodiment, the edit icon 216g may allow users to make corrections or updates as needed, maintaining the accuracy of the information. In an embodiment, the edit icon 216g may ensure that content remains current and can be easily adjusted as situations or data change. In an embodiment, the edit icon 216g may be a crucial tool for users who frequently update or revise their work.

Continuing reference to FIG. 2A, interactive element 216h may include information pertaining to a first data 168 corresponding to the node utilization interval. This interactive element may initially display a prompt box or placeholder text, giving users an overview or hint of the available information. Upon interaction, such as when the user clicks, taps, or hovers over the interactive element, the placeholder text may automatically disappear, making way for a detailed display of additional information. Once activated, interactive element 216h may dynamically expand or transition to reveal more comprehensive data, including information that identifies and details the plurality of datasets linked to the first projection structure. This first visual element may encompass various data points related to the node utilization interval, such as length of stay, usage of hospital resources, or the comparison of actual stay duration against projected or reimbursable intervals as defined by the entity duration value. The displayed information could include a breakdown of time intervals, statistical summaries, or graphical representations that enable users to understand the relationship between the patient's actual hospital stay and the expected or allowable duration. The interaction with element 216h may be enhanced by context-sensitive animations or transitions that guide the user's attention from the placeholder prompt to the expanded information view, ensuring a smooth and engaging user experience. Additionally, the element may be designed to display tooltip descriptions, expandable sections, or hover-over details that provide further clarity about each data subset in the first visual element, allowing users to explore data progressively without overwhelming them with too much information at once. To support ease of use, interactive element 216h may also be configured with icons, color-coded labels, or graphical indicators that help users quickly identify key data types, such as segments of the node utilization interval that are within reimbursable limits versus those that exceed coverage. These visual cues may improve interpretability and provide a more intuitive understanding of complex datasets. A dropdown icon 216k allows users to expand the first data, to provide more in-depth diagnosis, insurance, patient history, or other relevant data. By selecting this dropdown icon, users may access layered data without leaving the current interface, ensuring that critical contextual information is readily available.

Continuing reference to FIG. 2A, interactive element 216i includes a visual representation of a projected node utilization interval. This interactive element may represent the projected duration of an entity duration value of the node. This interactive element provides insight into the projected duration by offering a visual mapping of an entity's anticipated stay or interaction time within a specific node. In some embodiments, interactive element 216i may include diagrammatic or graphical representations similar to interactive element 216n, where portions of the visualization may be unshaded or colored differently to indicate the projected duration within the node. For instance, a shaded section could represent the estimated future interval, while any unshaded section might show the standard duration associated with similar entities at that node. This differentiation helps users quickly assess both the projected and typical duration values at a glance. Moreover, interactive element 216i may support user interactivity, allowing users to click or engage with portions of the visual representation to access more in-depth details, adjust projected intervals, or perform further actions.

Continuing reference to FIG. 2A, interactive element 216n includes a visual representation of the node utilization interval of the first data module. In an embodiment, interactive element 216n may include a graphical or diagrammatic representation of the plurality of inputs. In an embodiment, a shaded portion of a diagrammatic representation may represent the current duration of the patient's stay, or the current node utilization interval, whereas a non-shaded portion may represent a typical amount of time that a patient can stay at that particular hospital setting. The partly shaded portion of interactive element 216n may represent the projected amount of time that a patient will stay at the facility, or a predicted node utilization interval. The representation could be generated in real-time based on the plurality of inputs and may display various types of data, such as text summaries, charts, tables, or other visual representations of the system's response. The interactive element 216n may be interactive, allowing users to engage with the displayed information. For instance, users could click on specific elements within the diagrammatic representation, such as data points on a chart or text segments, to request additional details, perform follow-up actions, adjust node utilization interval, and the like. This interactive nature enables the response structure to serve not only as a display for the system's output but also as a hub for further user interaction, driving the flow of information based on evolving plurality of inputs. In some embodiments, the diagrammatic representation may be designed to dynamically update in response to changes in the plurality of inputs or the system's internal state. For example, if the user submits modifies parameters of the first data, the diagrammatic representation could be automatically refreshed to reflect the new data. The graphical elements within the structure, such as charts or tables, may be reconfigured to highlight relevant information or present new insights derived from the updated input.

Continuing reference to FIG. 2A, interactive element 216j functions as a response structure, designed to prompt the user to input specific data related to at least an entity duration value. The input field within interactive element 216j may include predefined suggestions, dropdown lists, or validation checks to ensure that the entered entity duration value aligns with standard reimbursement parameters and policy guidelines. For instance, if a user begins entering a duration, the response structure might display a range of typical values based on the patient's diagnosis, age, or insurance type, helping to reduce errors and streamline data entry. Once data is entered, interactive element 216j may validate the input against existing data within the system, cross-referencing it with patient-specific factors or default policy settings to confirm accuracy. This real-time validation ensures consistency and provides immediate feedback if there are any discrepancies, such as entering a value outside the allowable limits. Furthermore, after successful input, the entity duration value may be stored in the display data structure and subsequently used to calculate or update other metrics, such as node utilization intervals, directly influencing other visual indicators within the interface.

Figure 2B:
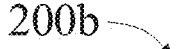
FIG. 2B is an exemplary illustration of a modified entity duration value in a graphical user interface.

Now referring to FIG. 2B, an exemplary illustration 200*b* of a modified entity duration value in graphical user interface is illustrated. Interactive element 216*k* may include information pertaining to the node utilization interval. When the user clicks or taps on the prompt box, the placeholder text may disappear and display more information identifying the modified node utilization interval related to the entity duration value. The second projection structure might also encompass data regarding insurance reimbursement limits, allowing the user to visually assess the alignment between the patient's current stay and the reimbursable duration.

In an embodiment, interactive element 216*l* may include a graphical or diagrammatic representation of the modified node utilization interval. In an embodiment, a shaded portion of a diagrammatic representation may represent the current duration of the patient's stay, or the current node utilization interval, whereas a non-shaded portion may represent a typical amount of time that a patient can stay at that particular hospital setting. In an embodiment, the shaded portion of interactive element 216*l* may display a color to identify which threshold category the modified node utilization interval falls within. For instance, if the shaded region indicates that the patient has spent more than the insurance allotted time in the facility, the shaded region will display a red coloring. The representation could be generated in real-time based on the plurality of inputs and may display various types of data, such as text summaries, charts, tables, or other visual representations of the system's response. The interactive element 216*i* may be interactive, allowing users to engage with the displayed information. For instance, users could click on specific elements within the diagrammatic representation, such as data points on a chart or text segments, to request additional details, perform follow-up actions, adjust node utilization interval, and the like.

Continuing reference to FIG. 2B, Interactive element 216*m* may be configured to display information specifically related to the entity duration value, which represents the maximum reimbursable duration for a patient's hospital stay as defined by their insurance provider or payor policy. Initially, this element may appear as a prompt box with placeholder text briefly indicating its purpose, providing users with a quick reference to the concept of reimbursable limits. When the user engages with interactive element 216*m* by clicking or tapping, the placeholder text disappears, revealing a more comprehensive view of the entity duration value and related information. This expanded display could include detailed breakdowns of the coverage limits based on the patient's age, diagnosis, or specific policy provisions, as well as any adjustments made to the entity duration value due to recent policy updates or specific patient circumstances. Additionally, interactive element 216*m* may offer insights into the patient's current utilization status, showing how much of the reimbursable duration has already been used and whether the remaining days are sufficient to cover the expected length of stay.

Figure 3:
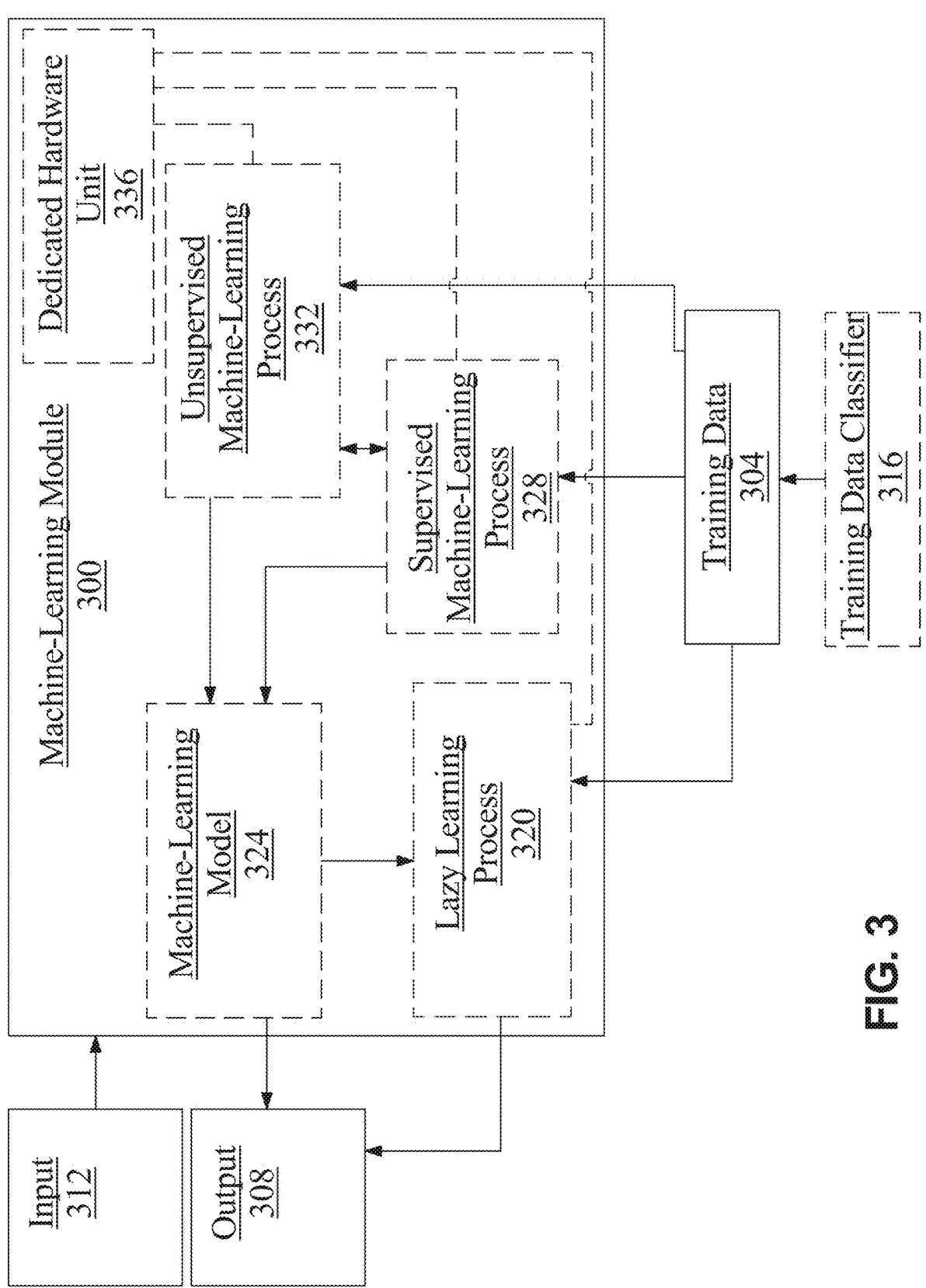
FIG. 3 is a block diagram of an exemplary machine-learning process.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. In a non-limiting embodiment, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; In a non-limiting embodiment, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, In a non-limiting embodiment by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; In a non-limiting embodiment, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, In a non-limiting embodiment, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example inputs such as user input and plurality of command input event handlers and outputs such as optimization datum.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to categories of historical reference data and categories of historical plurality of command input event handlers.

Still referring to FIG. 3, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)$ $P(A)+P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. In a non-limiting embodiment, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below.

Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. In a non-limiting embodiment, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, in a non-limiting embodiment, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. In a non-limiting embodiment, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, In a non-limiting embodiment, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. In a non-limiting embodiment, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. In a non-limiting embodiment, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. In a non-limiting embodiment, a computing device, processor, and/or module may convert a smaller number of units, such as in a low pixel count image, into a desired number of units, In a non-limiting embodiment by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, In a non-limiting embodiment by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, In a non-limiting embodiment as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $X_{max}$:

$$X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, In a non-limiting embodiment using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. In a non-limiting embodiment, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. In a non-limiting embodiment, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. In a non-limiting embodiment, a supervised learning algorithm may include user input and plurality of command input event handlers as described above as inputs, optimization datum as outputs, and a scoring function representing a desired form of relationship to be detected between inputs and outputs; scoring function may, In a non-limiting embodiment, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. In a non-limiting embodiment, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, In a non-limiting embodiment, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. In a non-limiting embodiment, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, system, system and/or module. In a non-limiting embodiment, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, system, and/or or method described in this disclosure; such examples may be modified and/or labeled according to user feedback or other processes to indicate desired results, and/or may have actual or measured results from a process being modeled and/or predicted by system, module, machine-learning model or algorithm, system, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, In a non-limiting embodiment, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, system, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
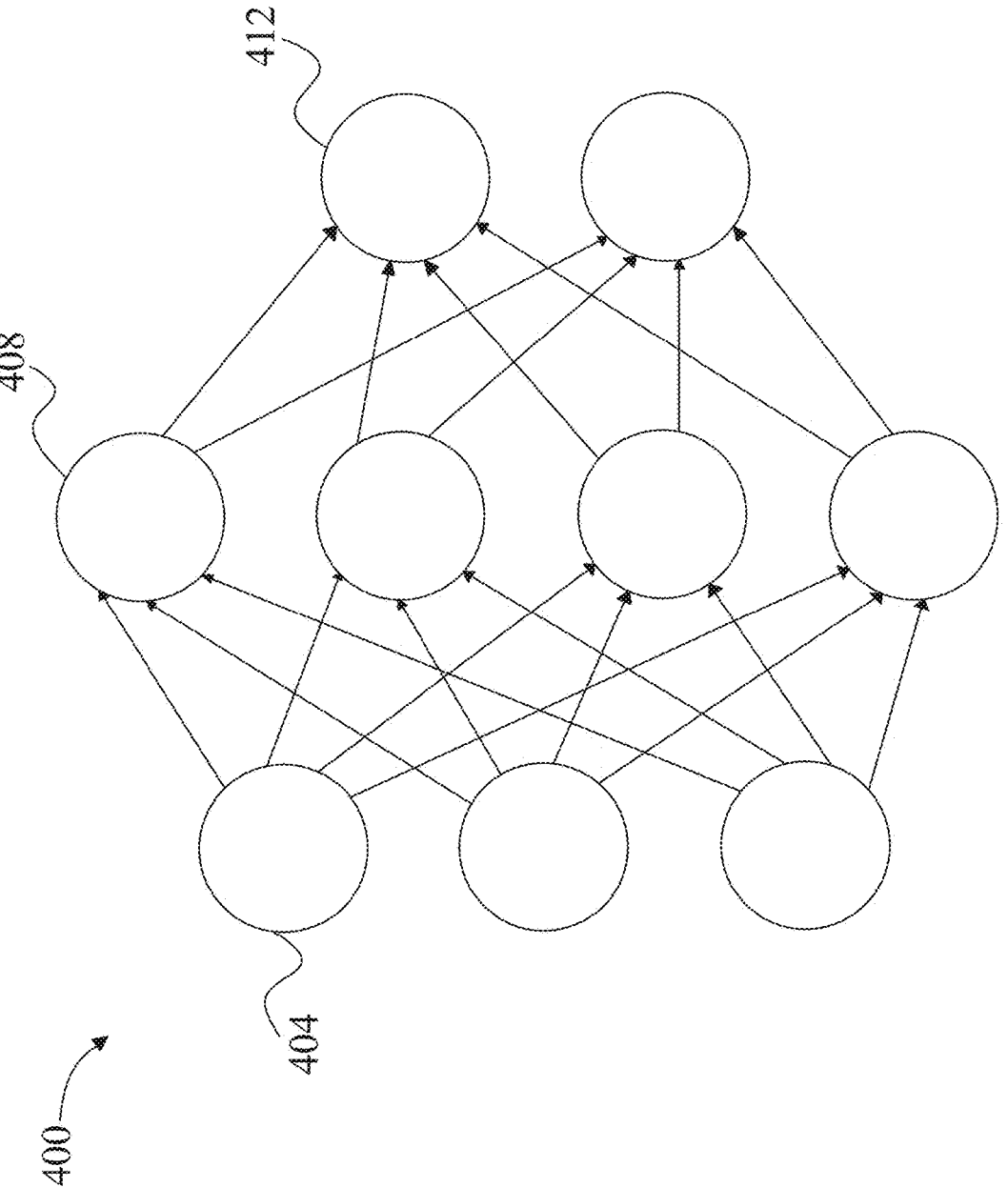
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
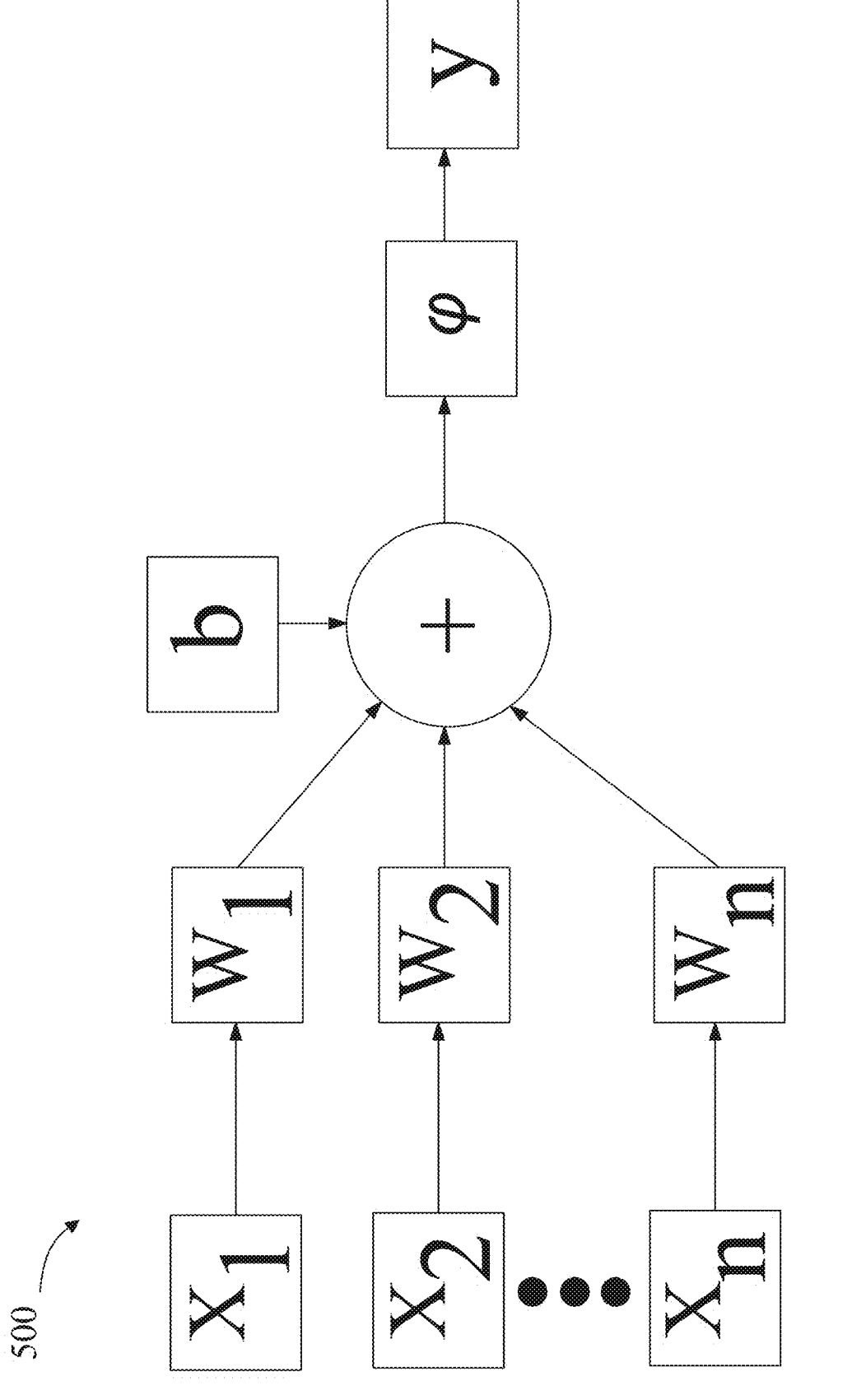
FIG. 5 is a diagram of an exemplary embodiment of a node of a neural network.

Referring now to FIG. 5, an exemplary embodiment of a node 500 of a neural network is illustrated. A node may include, without limitation, a plurality of inputs xi that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \ge 0 \\ \alpha(e^x - 1) \text{ for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are xi, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \ge 0 \end{cases}.$$

Fundamentally, there is no limit to the nature of functions of inputs xi that may be used as activation functions. As a non-limiting and illustrative example, node may perform a weighted sum of inputs using weights $w_i$ that are multiplied by respective inputs xi. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input xi may indicate whether the input is "excitatory," indicating that it has strong influence on the one or more outputs y, In a non-limiting embodiment by the corresponding weight having a large numerical value, and/or a "inhibitory," indicating it has a weak effect influence on the one more inputs y, In a non-limiting embodiment by the corresponding weight having a small numerical value. The values of weights $w_i$ may be determined by training a neural network using training data, which may be performed using any suitable process as described above.

Figure 6:
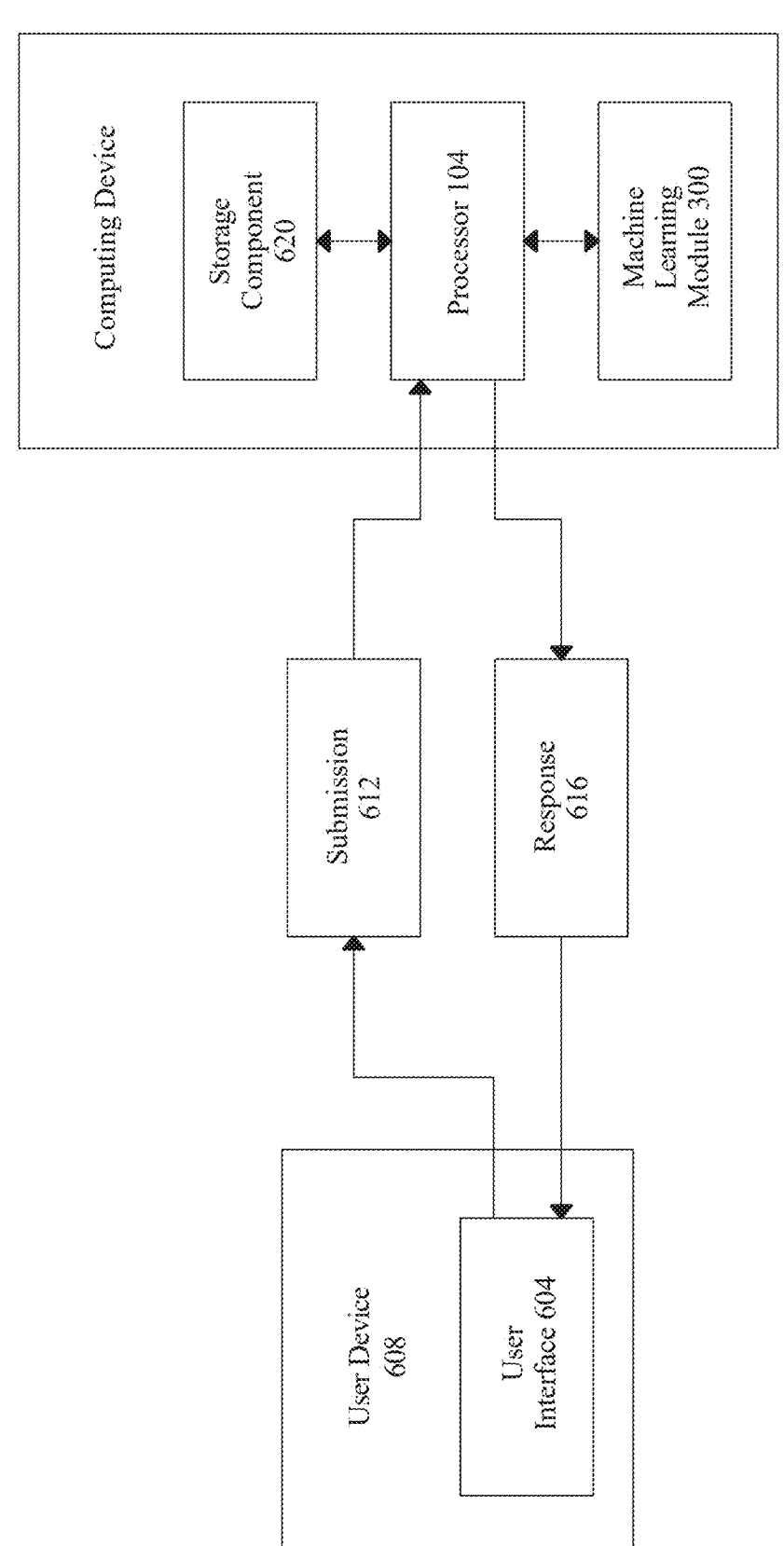
FIG. 6 is an exemplary embodiment of a chatbot system.

Referring now to FIG. 6, in one or more embodiments, system 100 may perform one or more of its functions, such as outputting at entity duration value implementing at least a chatbot system 600, an exemplary embodiment of which is schematically illustrated. In one or more embodiments, a user interface 604 may be communicatively connected with a computing device that is configured to operate a chatbot. In some cases, user interface 604 may be local to computing device. Alternatively, or additionally, in some other cases, user interface 604 may be remote to computing device, e.g., as part of a user device 608, and communicative with the computing device and processor 104 therein, by way of one or more networks, such as without limitation the internet. Alternatively, or additionally, user interface 604 may communicate with user interface 604 and/or computing device using telephonic devices and networks, such as without limitation fax machines, short message service (SMS), or multimedia message service (MMS). Commonly, user interface 604 may communicate with computing device using text-based communication, for example without limitation using a character encoding protocol, such as American Standard for Information Interchange (ASCII). Typically, user interface 604 may conversationally interface a chatbot, by way of at least a submission 612, from the user interface 604 to the chatbot, and a response 616, from the chatbot to the user interface 604. In many cases, one, or both, of submission 612 and response 616 are text-based communication. Alternatively, or additionally, in some cases, one or both of submission 612 and response 616 are audio-based communication.

With continued reference to FIG. 6, submission 612, once received by user interface 604 and/or computing device that operates a chatbot, may be processed by processor 104. In one or more embodiments, processor 104 may process submission 612 using one or more of keyword recognition, pattern matching, and natural language processing. In one or more embodiments, processor 104 may employ real-time learning with evolutionary algorithms. In one or more embodiments, processor 104 may retrieve a pre-prepared response from at least a storage component 620, based upon submission 612. Alternatively, or additionally, in one or more embodiments, processor 104 may communicate a response 616 without first receiving a submission 612, thereby initiating a conversation. In some cases, processor 104 may communicate an inquiry to user interface 604 and/or computing device, wherein processor 104 is configured to process an answer to the inquiry in a following submission 612 from the user interface 604 and/or computing device. In some cases, an answer to an inquiry presented within submission 612 from user interface 604 and/or computing device may be used by the computing device as an input to another function.

Now referring to FIG. 7, a flow diagram of an exemplary method for generating an entity duration value within a graphical user interface is illustrated. At step 705, method 700 includes generating a display data structure, using at least a processor. In an embodiment, generating the display data structure further includes providing a plurality of visual elements associated with a plurality of node modules and at least an event handler, wherein: a first visual element of the plurality of visual elements is linked to a first data module of a node module of the plurality of node modules; a second visual element of the plurality of visual elements is linked to a second data module of a node module of the plurality of node modules, wherein the second visual element comprises at least an entity duration value; the first data module is configured to: receive first data corresponding to a node utilization interval as a function of the at least an entity duration value and the plurality of node modules; and execute, using a first control structure, the second data module; and the second data module is configured to: modify the node utilization interval as a function of the at least an entity duration value. This may be implemented with reference to FIGS. 1-6.

Continuing reference to FIG. 7, at step 710, method 700 includes generating, by the at least a processor, the display data structure using the plurality of visual elements and the at least an event handler. This may be implemented with reference to FIGS. 1-6.

Continuing reference to FIG. 7, at step 715, method 700 includes configuring, using the display data structure, the display device to display the data structure. This may be implemented with reference to FIGS. 1-6.

Continuing reference to FIG. 7, at step 720, method 700 includes displaying, through a display device, the display data structure. This may be implemented with reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
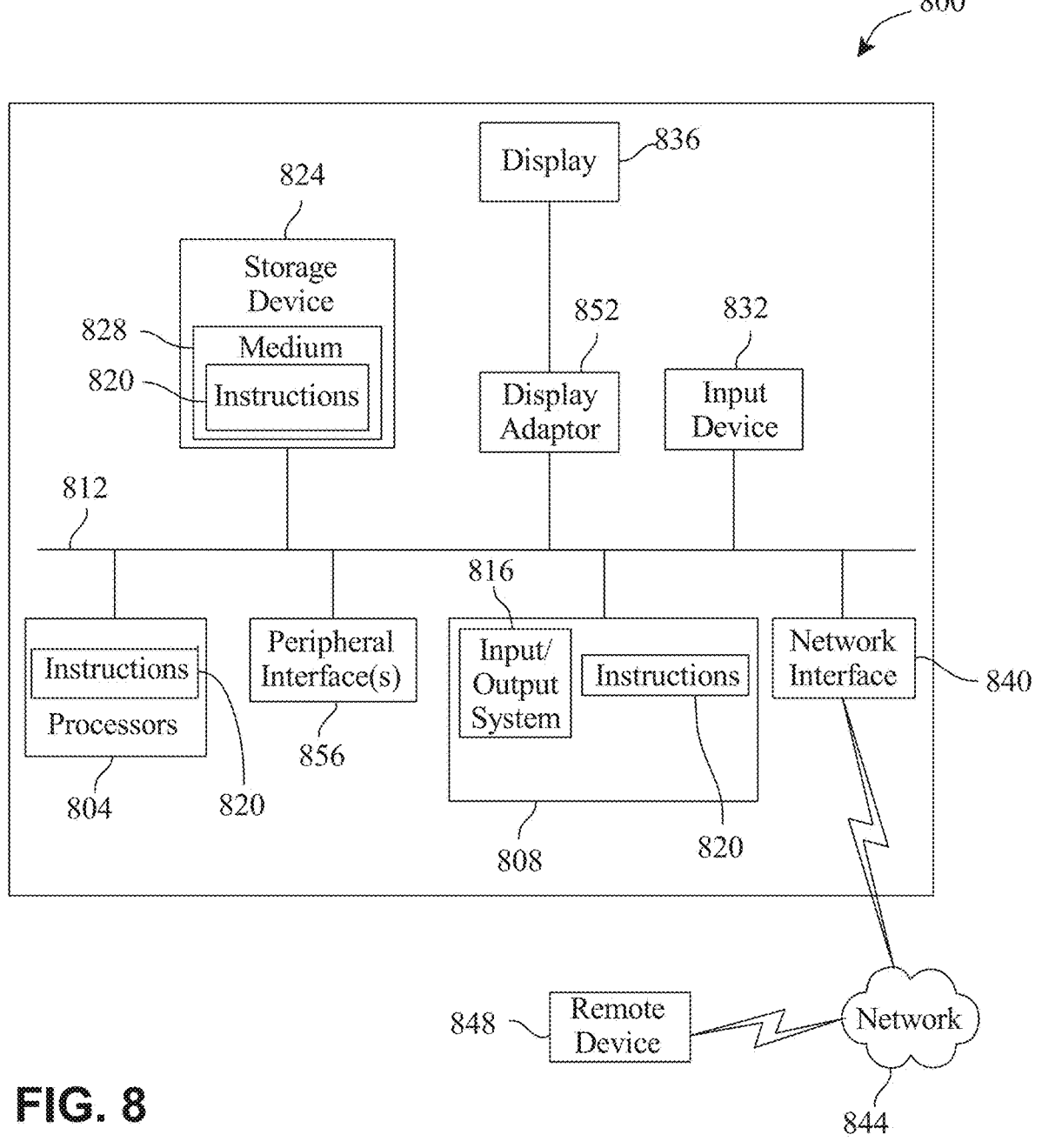
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display 836. Examples of a display device include, but are not limited to, a liquid crystal display (LCD), a cathode ray tube (CRT), a plasma display, a light emitting diode (LED) display, and any combinations thereof. Display adapter 852 and display 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating an entity duration value within a graphical interface, wherein the system comprises:

a display device, wherein the display device is configured to display a graphical user interface (GUI);

at least a computing device, wherein the computing device comprises:

a memory; and at least a processor, communicatively connected to the memory, wherein the at least a processor is configured to:

generate a display data structure, wherein generating the display data structure comprises:

providing a plurality of display data structure visual elements associated with a plurality of node modules and at least a display data structure event handler, wherein the plurality of node modules includes data structures comprising health and hospital-related information, wherein:

a first visual element of the plurality of display data structure visual elements is linked to a first data module of a first node module of the plurality of node modules;

a second visual element of the plurality of display data structure visual elements is linked to a second data module of a second node module of the plurality of node modules;

the first data module comprises a first structured component encapsulating data handling of a first set of data and is configured to:

receive, using at least a chatbot interface of the display device, first data corresponding to a node utilization interval as a function of at least an entity duration value and the plurality of node modules, wherein the chatbot interface operates on the display device and is configured to process the first data using natural language processing; and execute, using a first control structure of a control structure, the second data module; and the second data module comprises a second structured component encapsulating data handling of a second set of data and is configured to:

modify, using a second control structure of the control structure, the node utilization interval as a function of the at least an entity duration value, wherein the at least an entity duration value is a data metric representing a reimbursable duration of a patient's hospital stay covered by an insurance provider;

classifying the modified node utilization interval into one of a plurality of threshold categories, wherein the classification triggering automated notifications and predictive updates to discharge planning which further causes event-driven refresh of affected visual elements and propagation of any adjustments made within the display data structure back to the plurality of node modules through bi-directional data binding:

generating the display data structure using the plurality of display data structure visual elements and the at least a display data structure event handler; and display, using the display device, the display data structure.

2. The system of claim 1, wherein generating the display data structure comprises classifying the modified node utilization interval into a threshold category.

3. The system of claim 2, wherein classifying the modified node utilization interval comprises using a modified node utilization interval classifier to correlate the modified node utilization interval and the at least an entity duration value.

4. The system of claim 2, wherein generating the display data structure comprises assigning a value encoded score for each modified node utilization interval of a plurality of modified node utilization intervals as a function of the modified node utilization interval classifier.

5. The system of claim 1, wherein the memory contains instructions further configuring the at least a processor to iteratively update, using the display data structure event handler, the display data structure based on new data associated with at least one of the first node module and the second node module.

6. The system of claim 1, wherein the first control structure comprises a set of instructions stored in the memory, wherein the set of instructions direct the first data module, when executed by the at least a processor, to initiate at least a command within the second data module.

7. The system of claim 1, wherein receiving the first data corresponding to the node utilization interval comprises selecting, using the at least a processor, cluster-node modules comprising one or more node modules, wherein each cluster of the cluster-node module comprises at least a common parameter of at least one of the first node module and the second node module.

8. The system of claim 7, further comprising selecting, using a cluster-node machine learning model, the cluster-node modules, wherein the cluster-node machine learning model is trained using cluster-node training data to correlate at least one of the first node module and the second node module to at least one of the cluster-node modules.

9. A method for generating an entity duration value within a graphical interface, wherein the method comprises:

generating, using at least a processor, a display data structure, wherein generating the display data structure comprises:

providing a plurality of display data structure visual elements associated with a plurality of node modules and at least a display data structure event handler, wherein the plurality of node modules includes data structures comprising health and hospital-related information, wherein:

a first visual element of the plurality of display data structure visual elements is linked to a first data module of a first node module of the plurality of node modules, wherein the first data module comprises a first structured component encapsulating data handling of a first set of data;

a second visual element of the plurality of display data structure visual elements is linked to a second data module of a second node module of the plurality of node modules, wherein the second data module comprises a second structured component encapsulating data handling of a second set of data; and receiving, using the first data module and at least a chatbot interface of a display device, first data corresponding to a node utilization interval as a function of at least an entity duration value and the plurality of node modules, wherein the chatbot interface operates on the display device and is configured to process the first data using natural language processing;

executing, using the first data module and a first control structure of a control structure, the second data module;

modifying, using the second data module and a second control structure of the control structure, the node utilization interval as a function of the at least an entity duration value, wherein the at least an entity duration value is a data metric representing a reimbursable duration of a patient's hospital stay covered by an insurance provider;

classifying the modified node utilization interval into one of a plurality of threshold categories, wherein the classification triggering automated notifications and predictive updates to discharge planning which further causes event-driven refresh of affected visual elements and propagation of any adjustments made within the display data structure back to the plurality of node modules through bi-directional data binding;

generating the display data structure using the plurality of display data structure visual elements and the at least a display data structure event handler; and generating the display data structure using the plurality of display data structure visual elements and the at least a display data structure event handler; and displaying, using the display device, the display data structure.

10. The method of claim 9, wherein generating the display data structure comprises classifying the modified node utilization interval into a threshold category.

11. The method of claim 10, wherein classifying the modified node utilization interval comprises using a modified node utilization interval classifier to correlate the modified node utilization interval and the at least an entity duration value.

12. The method of claim 10, wherein generating the display data structure comprises assigning a value encoded score for each modified node utilization interval of a plurality of modified node utilization intervals as a function of the modified node utilization interval classifier.

13. The method of claim 9, wherein the method further comprises to iteratively updating, using the at least a processor and the display data structure event handler, the display data structure based on new data associated with at least one of the first node module and the second node module.

14. The method of claim 9, wherein the first control structure comprises a set of instructions stored in a memory communicatively connected to the at least a processor, wherein the set of instructions direct the first data module, when executed by the at least a processor, to initiate at least a command within the second data module.

15. The method of claim 9, wherein receiving the first data corresponding to the node utilization interval comprises selecting, using the at least a processor, cluster-node modules comprising one or more node modules, wherein each cluster of the cluster-node module comprises at least a common parameter of at least one of the first node module and the second node module.

16. The method of claim 15, further comprising selecting, using a cluster-node machine learning model, the cluster-node modules, wherein the cluster-node machine learning model is trained using cluster-node training data to correlate at least one of the first node module and the second node module to at least one of the cluster-node modules.

\* \* \* \* \* 20